US00PP30493P2

(12) United States Plant Patent
Bron

(10) Patent No.: US PP30,493 P2
(45) Date of Patent: May 14, 2019

(54) ***COTONEASTER* PLANT NAMED 'BRONFIRE'**

(50) Latin Name: ***Cotoneaster* hybrid**
Varietal Denomination: Bronfire

(71) Applicant: Vincent Bron, Grand Forks (CA)

(72) Inventor: Vincent Bron, Grand Forks (CA)

( * ) Notice: Subject to any disclaimer, the term of this patent is extended or adjusted under 35 U.S.C. 154(b) by 76 days.

(21) Appl. No.: 15/530,937

(22) Filed: Mar. 27, 2017

(51) Int. Cl.
*A01H 5/00* (2018.01)

(52) U.S. Cl.
USPC ..... Plt./226

(58) Field of Classification Search
USPC ..... Plt./226
See application file for complete search history.

(56) References Cited

PUBLICATIONS

First Editions Plants. 'Autumn Fire' *Cotoneaster*. http://www.firsteditionsplants.com/the-plants/shrubs/autumn-fire-cotoneaster. 1 page.*

Oregon State, College of Agricultural Sciences, Dept of Horticulture. Citation for 'Autumn Fire'. https://landscapeplants.oregonstate.edu/plants/cotoneaster-salicifolius-autumn-fire. 1 page.*

* cited by examiner

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Cotoneaster* named 'Bronfire', characterized by its foliage that is dark green in color that changes to orange and red in color in the fall, its foliage that is glossy, cup-shaped and slightly twisted, its mid to late summer berries that are bright red in color, its upright pant habit and its cold hardiness at least to U.S.D.A. Zone 3.

2 Drawing Sheets

Botanical classification: *Cotoneaster* hybrid.
Cultivar designation: 'Bronfire'.

BACKGROUND OF THE INVENTION

The present invention relates to a new and distinct cultivar of *Cotoneaster* plant of hybrid origin, botanically known as *Cotoneaster* 'Bronfire', and will be referred to hereafter by its cultivar name, 'Bronfire'. 'Bronfire' is a new cultivar of deciduous shrub grown for use as a landscape plant.

The new cultivar originated as a chance seedling growing in a container during production at a nursery in Grand Forks, B. C, Canada in summer of 2010. The container originated from seed planted from an unnamed and unpatented plant of *Cotoneaster lucidus*. The male parent is unknown, however it is thought to be a plant of *Cotoneaster apiculatas* based on the characteristic of the new cultivar.

Asexual propagation of the new cultivar was first accomplished by softwood stem cuttings in Grand Forks, British Columbia, Canada in 2011 by the Inventor. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics 'Bronfire'. These attributes in combination distinguish 'Bronfire' as a new and distinct cultivar of *Cotoneaster*.

1. 'Bronfire' exhibits foliage that is intense dark green in color that changes to orange and red in color in the fall.
2. 'Bronfire' exhibits foliage that is glossy, cup-shaped and slightly twisted.

3. 'Bronfire' exhibits mid to late summer berries that are bright red in color.
4. 'Bronfire' exhibits blooms that are pink-white in color in late spring.
5. 'Bronfire' exhibits an upright plant habit.
6. 'Bronfire' exhibits cold hardiness at least to U.S.D.A. Zone 3.

The female parent plant is similar to 'Bronfire' in having an upright plant habit. The female parent differs from 'Bronfire' in having berries that are black in color and foliage that is lighter in color and flat in aspect. 'Bronfire' can be most closely compared to typical plants of *Cotoneaster apiculatus* (and probably species of the male parent). Typical plants of *Cotoneaster apiculatus* are similar to 'Bronfire' in having berries that are red in color and glossy foliage. *Cotoneaster apiculatus* differs from 'Bronfire' in having foliage that is smaller in size and in having a spreading plant habit. 'Bronfire' can also be compared to the *Cotoneaster* cultivar 'Tom Thumb' (not patented). 'Tom Thumb' differs from 'Bronfire' in being a groundcover type *Cotoneaster*. There are no known cultivars known to the Inventor of a hybrid between *Cotoneaster lucidus* and *Cotoneaster apiculatus*.

BRIEF DESCRIPTION OF THE DRAWINGS

The accompanying colored photographs illustrates the overall appearance and distinct characteristics of the new *Cotoneaster*. The photographs were taken of plants 3 years in age as grown outdoors in Grand Forks, British Columbia, Canada.

The photograph in FIG. 1 provides a close up view of the foliage turning in fall of 'Bronfire'.

Figure 1:
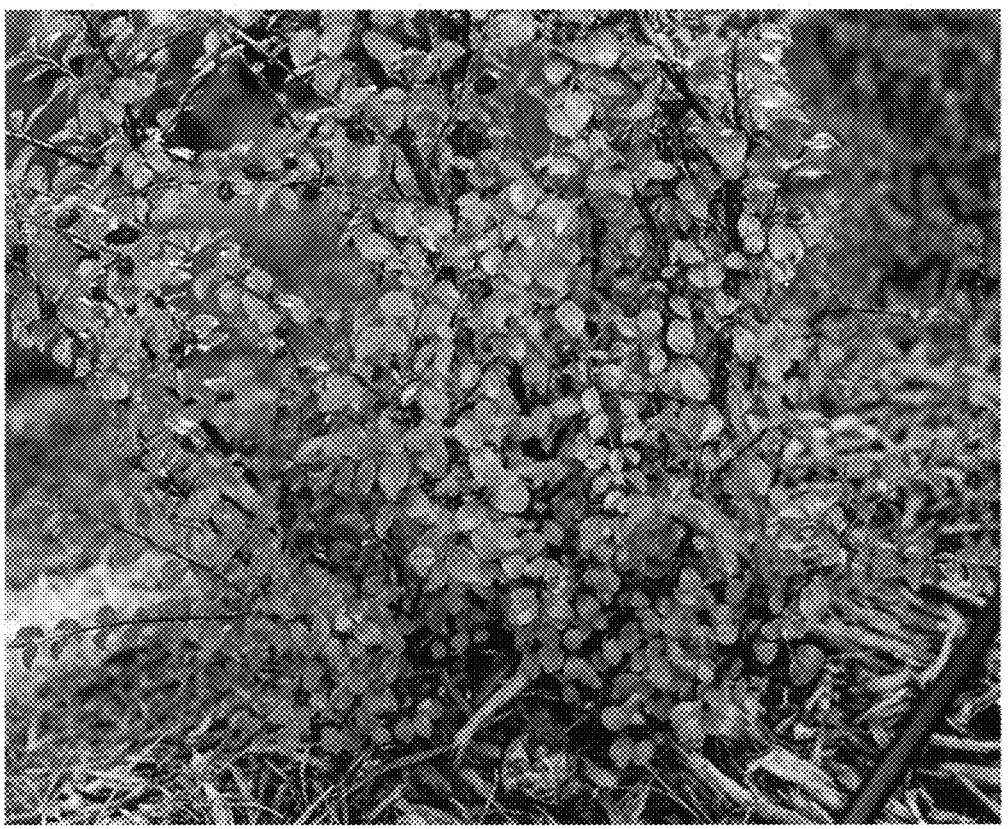
Figure 2:
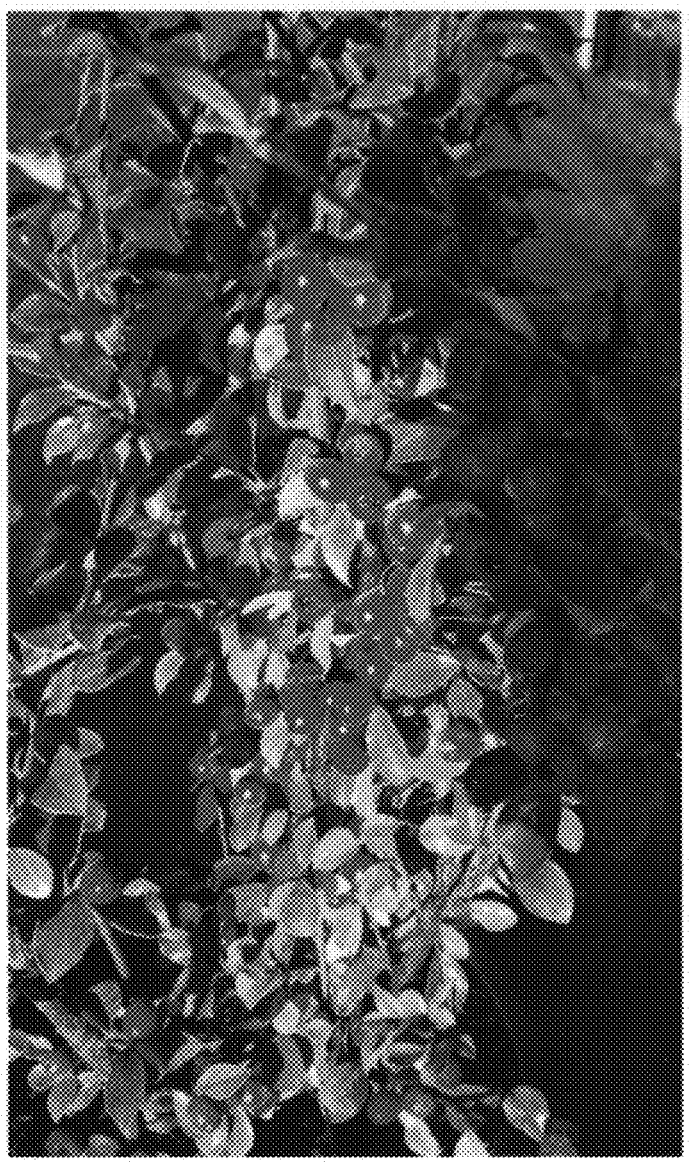

The photograph in FIG. 2 provides a view of the berries of 'Bronfire'.

The colors in the photographs are as close as possible with the digital photography and printing techniques utilized and the color codes in the detailed botanical description accurately describe the new *Cotoneaster*.

DETAILED BOTANICAL DESCRIPTION OF THE PLANT

The following is a detailed description of 3 year-old plants of the new cultivar as grown in two-gallon containers outdoors in Grand Forks, British Columbia, Canada. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General characteristics:

*Blooming period*.—Late spring in British Columbia, Canada.

*Plant type*.—Deciduous shrub.

*Plant habit*.—Upright.

*Height and spread*.—Reaches 1.82 m in height and spread in the landscape.

*Hardiness*.—At least to U.S.D.A. Zone 3.

*Diseases*.—No susceptibility or resistance to diseases has been observed.

*Root development*.—About 3 to 4 week to initiate roots and 60 to 90 days to produce a young rooted plant in a plug.

*Propagation*.—Softwood stem cuttings.

*Growth rate*.—Moderately vigorous.

Stem description:

*Shape*.—Round.

*Stem color*.—Ranging between 200B and 200D.

*Stem size*.—Lateral branches; up to about 60 cm in length and 3 mm in width.

*Stem surface*.—Glossy and slightly rugose, woody.

*Internode length*.—An average of 2 cm.

*Branching*.—Freely branched with main shoots growing from the base, average of 10 main stems.

*Stem strength*.—Very Strong.

Foliage description:

*Leaf shape*.—Obtuse.

*Leaf division*.—Single.

*Leaf base*.—Cuneate.

*Leaf apex*.—Obtuse.

*Leaf fragrance*.—None.

*Leaf venation*.—Pinnate, both surface veins match leaf color.

*Leaf margins*.—Entire and puberulent.

*Leaf arrangement*.—Alternate, in clusters.

*Leaf attachment*.—Petiolate.

*Leaf quantity*.—Average of 4 to 5 leaves per cluster, Average of 56 leaves per lateral branch 27 cm in length.

*Leaf surface*.—Upper surface is glossy and puberlent, lower surface is dull and puberulent.

*Leaf size*.—Up to about 2.5 cm in length, up to 1.5 cm in width.

*Leaf color*.—Spring; young and mature upper surface; 143A and NN137A, young and mature lower surface; N148A, fall; upper surface a blend of 143A and N45A and 45A and 40A, lower surface a blend of N148A and 39A to 39A and 42A.

*Petioles*.—Up to 6 mm in length, 2 mm in width, puberulent surface, N144A in color.

Inflorescence description:

*Inflorescence type*.—Clusters on terminals and upper axils of main stems and lateral and tertiary branches.

*Inflorescence size*.—1 cm in length and diameter.

*Inflorescence number*.—Average of 13 per lateral branch 27 cm in length.

*Flower number*.—Average of 3 to 4 per cluster.

*Flower fragrance*.—Faint.

*Inflorescence longevity*.—About 5 weeks in the landscape.

*Flower type*.—Cup shaped with base of corolla and fused to calyx.

*Flower size*.—Average of 5 mm in width and depth.

*Peduncles*.—Average of 4 mm in length and 1 mm in diameter, N144A in color, surface is puberulent.

*Flower buds*.—Globose-obovate in shape, an average of 3 mm in length and width, color; a blend of NN155D and 63A.

*Calyx*.—Campanulate and narrowing to tube (hypanthium), width; average of 5 mm, depth; including tube portion 5 mm, puberulent surface, N144A in color.

*Sepals*.—5, fused with free apex an average of 2 mm in depth and width, margin entire and heavily puberulent, inner and outer surfaces waxy and heavily puberulent, color of outer surface N144A, color of inner surface 184A.

*Petals*.—5, orbicular in shape, slightly overlapping, cupped, margin entire to wavy, base cuneate and fused to calyx, apex is rounded, average of 5 mm in length and 4 mm in width, early spring; color when opening and fully open inner and outer surface; a blend of NN155D and 63A, surface glabrous on inner and outer surface.

Reproductive organs:

*Pistils*.—1, stigma; minute, style; average of 2 mm in length and 0.5 mm in width and 145B in color, ovary is conical-shaped, 1 mm in length and width and 145B in color.

*Stamens*.—10, with 10 infertile stamenoids arranged between stamens, filaments are round in shape, up to 3 mm in length and 0.5 mm in width and 63A in color, anthers are an average of 0.5 mm in diameter and 8D in color, pollen is moderate and 8B in color, stamenoids; triangular in shape, average of 0.5 mm in length, NN155D in color.

*Fruit and seed*.—Hips produced in late summer; an average of 3 per leaf cluster, held at an upright angle, firm, an average of 9 mm in length and 5 mm in diameter, color; 45A, turning to 53A as it matures, oblong in shape with a rounded apex that consists of 5 lobes that are an average of 1 mm in length, acute apex and cuneate base, shiny and smooth surface, seed; 1 seed produced in each berry, 5 mm in diameter, hard, 161A in color, surface is wavy and rough.

It is claimed:

1. A new and distinct cultivar of *Cotoneaster* plant named 'Bronfire' as herein illustrated and described.

* * * * *